United States Patent [19]

Sancoff et al.

[11] Patent Number: 5,553,741
[45] Date of Patent: Sep. 10, 1996

[54] LIQUID DELIVERY DEVICE

[75] Inventors: Gregory E. Sancoff, Rancho Santa Fe; Mark C. Doyle, San Diego, both of Calif.

[73] Assignee: River Medical, Inc., San Diego, Calif.

[21] Appl. No.: 372,818

[22] Filed: Dec. 23, 1994

Related U.S. Application Data

[62] Division of Ser. No. 105,327, Aug. 6, 1993, Pat. No. 5,398,851.

[51] Int. Cl.⁶ .................................................... B65D 83/14
[52] U.S. Cl. .......................... 222/1; 222/386.5; 222/399; 604/141; 604/145
[58] Field of Search .......................... 222/1, 386.5, 394, 222/399, 95; 604/131, 141, 145

[56] References Cited

U.S. PATENT DOCUMENTS

| | | |
|---|---|---|
| 754,037 | 3/1904 | Anderson . |
| 1,469,501 | 10/1923 | Dollin . |
| 1,731,767 | 10/1929 | Cramer . |
| 1,832,817 | 11/1931 | Pearsons . |
| 2,105,690 | 1/1938 | Greenblatt . |
| 2,312,381 | 3/1943 | Bickenheuser . |
| 2,381,749 | 8/1945 | Hull . |
| 2,473,912 | 6/1949 | Schwinn . |
| 2,759,337 | 8/1956 | Katz . |
| 2,815,152 | 12/1957 | Mills . |
| 2,845,090 | 7/1958 | Rost . |
| 2,912,018 | 11/1959 | Leech . |
| 3,022,785 | 2/1962 | Crockford et al. ............... 604/145 X |
| 3,023,750 | 3/1962 | Baron . |
| 3,053,422 | 9/1962 | Tenison et al. . |
| 3,096,000 | 7/1963 | Staley . |
| 3,122,181 | 2/1964 | Hebenstreit et al. . |
| 3,146,169 | 8/1964 | Stephenson et al. . |
| 3,153,414 | 10/1964 | Beall et al. . |
| 3,175,558 | 3/1965 | Caillouette et al. . |
| 3,178,075 | 4/1965 | Riedl et al. . |
| 3,217,947 | 11/1965 | Bauerlein . |
| 3,357,601 | 12/1967 | Crawford et al. . |
| 3,367,545 | 2/1968 | Cook . |
| 3,384,113 | 5/1968 | Pennisi . |
| 3,385,481 | 5/1968 | Frangos . |
| 3,405,845 | 10/1968 | Cook et al. . |
| 3,429,672 | 2/1969 | Young . |
| 3,468,308 | 9/1969 | Bierman . |
| 3,577,512 | 5/1971 | Shepherd et al. . |
| 3,585,982 | 6/1971 | Hollinshead . |

(List continued on next page.)

FOREIGN PATENT DOCUMENTS

| | | | |
|---|---|---|---|
| 2159523 | 6/1973 | France | ................................ 604/145 |
| WO9207612 | 5/1992 | WIPO . | |
| WO9325269 | 12/1993 | WIPO . | |

*Primary Examiner*—Kevin P. Shaver
*Attorney, Agent, or Firm*—Knobbe, Martens, Olson & Bear

[57] ABSTRACT

A liquid dispensing device and the method of dispensing liquid are disclosed. The device is uniquely suited to meet the requirements of hospitals and other institutions for long shelf life in inert-condition and ready activation when needed. The device includes a hollow gas- and liquid-tight casing (preferably spherical or cylindrical), a flexible gas- and liquid-tight membrane disposed entirely across the casing interior dividing the interior into a propellant chamber and a liquid chamber; an outlet port from the liquid chamber; two mutually reactive chemicals in the propellant chamber but separated by a barrier; and a member to breach the barrier and permit the chemicals to come into contact; the two chemicals being reactive upon contact to form a propellant gas. The propellant gas thereupon expands against the membrane, moves the membrane to enlarge the propellant chamber, decrease the liquid chamber, and expel the contained liquid from the liquid chamber through the outlet port. The barrier may be breached in any convenient manner, as by breaking a frangible barrier or perforating a perforable one. Preferably at least one of the chemicals is in liquid form, and one is a Group I or II metal carbonate or bicarbonate while the other is an acid, acid anhydride or acid salt; the most preferred combination is sodium carbonate and citric acid.

6 Claims, 7 Drawing Sheets

U.S. PATENT DOCUMENTS

| | | |
|---|---|---|
| 3,640,277 | 2/1972 | Adelberg . |
| 3,662,929 | 5/1972 | Sims . |
| 3,667,652 | 6/1972 | Morane . |
| 3,708,089 | 1/1973 | Holder . |
| 3,718,236 | 2/1973 | Reyner et al. . |
| 3,736,930 | 6/1973 | Georgi . |
| 3,756,556 | 9/1973 | Georgi . |
| 3,800,794 | 4/1974 | Georgi . |
| 3,804,077 | 4/1974 | Williams . |
| 3,840,009 | 10/1974 | Michaels et al. . |
| 3,894,538 | 7/1975 | Richter . |
| 3,949,911 | 4/1976 | Morane ............................ 222/386.5 |
| 3,993,061 | 11/1976 | O'Leary . |
| 3,994,294 | 11/1976 | Knute . |
| 4,037,598 | 7/1977 | Georgi . |
| 4,049,158 | 9/1977 | Lo et al. . |
| 4,067,332 | 1/1978 | O'Leary . |
| 4,080,967 | 3/1978 | O'Leary . |
| 4,111,613 | 9/1978 | Sperry . |
| 4,137,913 | 2/1979 | Georgi . |
| 4,203,441 | 5/1980 | Theeuwes . |
| 4,222,127 | 9/1980 | Donachy . |
| 4,235,236 | 11/1980 | Theeuwes . |
| 4,237,881 | 12/1980 | Beigler et al. . |
| 4,331,728 | 5/1982 | Theeuwes . |
| 4,335,835 | 6/1982 | Beigler . |
| 4,353,887 | 10/1982 | Hess . |
| 4,360,131 | 11/1982 | Reyner . |
| 4,373,341 | 2/1983 | Mahaffy et al. . |
| 4,376,500 | 3/1983 | Banks et al. . |
| 4,379,453 | 4/1983 | Baron . |
| 4,382,965 | 5/1983 | Sandine et al. . |
| 4,468,220 | 8/1984 | Willbanks ............................ 604/145 X |
| 4,478,044 | 10/1984 | Magid . |
| 4,491,250 | 1/1985 | Liebermann . |
| 4,507,116 | 3/1985 | Leibinsohn . |
| 4,510,734 | 4/1985 | Banks et al. . |
| 4,511,355 | 4/1985 | Franetzki . |
| 4,513,884 | 4/1985 | Magid . |
| 4,518,103 | 5/1985 | Lim et al. . |
| 4,553,685 | 11/1985 | Magid . |
| 4,567,948 | 2/1986 | Rozniecki . |
| 4,581,014 | 4/1986 | Millerd et al. . |
| 4,597,959 | 7/1986 | Barr . |
| 4,618,487 | 10/1986 | DuBois . |
| 4,626,241 | 12/1986 | Campbell . |
| 4,629,620 | 12/1986 | Lindahl et al. . |
| 4,640,445 | 2/1987 | Yamada . |
| 4,646,946 | 3/1987 | Reyner . |
| 4,648,955 | 3/1987 | Maget . |
| 4,663,147 | 5/1987 | DePrince . |
| 4,673,392 | 6/1987 | Keime . |
| 4,675,020 | 6/1987 | McPhee . |
| 4,679,706 | 7/1987 | Magin et al. . |
| 4,687,423 | 8/1987 | Maget et al. . |
| 4,687,660 | 8/1987 | Baker . |
| 4,734,092 | 3/1988 | Millerd . |
| 4,780,117 | 10/1988 | Lahey . |
| 4,802,343 | 2/1989 | Rudick . |
| 4,804,366 | 2/1989 | Zdeb et al. . |
| 4,816,262 | 3/1989 | McMullen . |
| 4,847,093 | 7/1989 | Ayer . |
| 4,850,978 | 7/1989 | Dudar et al. . |
| 4,886,541 | 12/1989 | Maget . |
| 4,893,730 | 1/1990 | Bolduc ............................ 222/145 X |
| 4,896,794 | 1/1990 | Banks et al. ............................ 222/386.5 X |
| 4,898,209 | 2/1990 | Zbed . |
| 4,902,278 | 2/1990 | Maget et al. . |
| 4,923,095 | 5/1990 | Dorfman et al. . |
| 4,936,829 | 6/1990 | Zbed et al. . |
| 5,009,340 | 4/1991 | Morane ............................ 222/94 |
| 5,022,564 | 6/1991 | Reyner . |
| 5,024,657 | 6/1991 | Needham et al. . |
| 5,035,230 | 7/1991 | Steidl . |
| 5,035,351 | 7/1991 | Moran ............................ 222/394 |
| 5,049,129 | 9/1991 | Zbed et al. . |
| 5,054,651 | 10/1991 | Morane . |
| 5,080,652 | 1/1992 | Sancoff et al. . |
| 5,090,963 | 2/1992 | Gross et al. . |
| 5,101,730 | 4/1992 | Bender . |
| 5,106,374 | 4/1992 | Apperson et al. . |
| 5,116,316 | 5/1992 | Sertic et al. . |
| 5,137,186 | 8/1992 | Moran . |
| 5,163,909 | 11/1992 | Stewart ............................ 604/131 X |
| 5,167,631 | 12/1992 | Thompson et al. . |
| 5,169,389 | 12/1992 | Kriesel ............................ 604/131 X |
| 5,179,982 | 1/1993 | Bérubé et al. ............................ 222/386.5 X |
| 5,242,406 | 9/1993 | Gross et al. ............................ 604/141 X |
| 5,312,389 | 5/1994 | Theeuwes et al. ............................ 604/141 X |
| 5,318,557 | 6/1994 | Gross ............................ 604/141 X |
| 5,333,763 | 8/1994 | Lane et al. ............................ 222/386.5 |
| 5,398,850 | 3/1995 | Sancoff et al. ............................ 222/386.5 |
| 5,398,851 | 3/1995 | Sancoff et al. ............................ 222/386.5 |

Fig. 20B

LIQUID DELIVERY DEVICE

RELATED APPLICATIONS

This application is a divisional application of U.S. application Ser. No. 08/105,327, filed Aug. 6, 1993, now U.S. Pat. No. 5,398,851.

BACKGROUND OF THE INVENTION

1. Field of the Invention

The present invention relates to a method and apparatus that provide for the controlled delivery of a liquid to a patient. In particular, the invention relates to the controlled delivery of a liquid, preferably including a medication, into a patient with an infusion pump that is operated by gas pressure.

2. Description of the Prior Art

The controlled delivery of liquids, particularly those containing medications, to patients has received substantial attention in the medical arts. The concept of drug infusion is that a patient can be given a medication over a given, relatively prolonged, time period. In this manner, the need for repeated injections is eliminated and there is a reduced risk of a development of drug sensitivities. Moreover, it is widely believed that sustained treatment with a drug is generally more effective than single bolus treatment. Further, infusion pump type devices allow for ambulatory treatment of a patient; i.e., the patient need not be attached to an intravenous ("IV") stand and bag.

There have been a number of products in the past which have been useful for delivering liquids, such as medications, at a controlled flow rate. A typical example, which has been quite successful commercially, is illustrated in U.S. Pat. No. 5,080,652 to Sancoff et al. There has been a tendency for the art to focus on ambulatory care concerns. For example, many devices have been developed primarily for use by a patient. The patient can administer the drug to themselves over a prolonged time period without a hospital stay.

Less emphasis has been directed to institutional use (such as use in hospitals). However, for the most part, these devices have failed to provide for an important need of such institutions where long-term storage and subsequent ready availability of medications is important.

Devices such as the previously mentioned Sancoff et al. product have been designed and intended for use shortly after preparation. The devices are filled and soon thereafter connected to the patient, usually through an intravenous tube, and the medication is then administered to the patient by the fluid flow and metering components of the particular device. For instance, in the above-mentioned Sancoff et al. device, the liquid is dispensed or delivered from the device through the action of elasticized membranes which push the liquid containing the medication from the device to the patient. Other products from the prior art use compressed gas to force the medication or other liquid from a container. See, for example, U.S. Pat. No. 5,106,374 to Apperson et al.

Such products, while useful for their purpose of prompt administration of medication to patients, are not amenable to preparation and extended storage of medication for subsequent use. In devices where the medication or other liquid is under constant pressure for an extended period of time, as from a compressed gas or a stressed resilient membrane, the pressure tends to drop, as the elastic material loses resiliency or as the compressed gas reacts with the liquid or leaks from the container. Further, such devices generally require complicated valving to retain the liquid under pressure and prevent leakage, which adds significantly to the cost and complexity of the individual products.

Other devices have attempted to circumvent these problems by requiring pressurization at the time that the device is intended to be used. Such devices, however, have been cumbersome and not readily usable. They normally require an external source of pressurization such as attachment to a carbon dioxide cartridge or other outside gas generation equipment. It is time-consuming to obtain such equipment, to connect it to the device, and to wait for the pressurization to be completed. Where medication is needed quickly, the time delay can present a significant danger to a patient.

The prior-art has also attempted to make use of on-the-spot gas generation through the use of the reaction of chemicals that generate gas upon contact. See, for example, U.S. Pat. No. 3,023,750, to Baron. The generated gas, then, was used to force a liquid from a bag for delivery to a patient. However, this invention fails to provide the control that is essential to infusion. Gas is generated very rapidly, causing rapid flow rates and high pressure.

A variety of patents for spray type canisters have used chemical reactions to generate a gas for a propellant to drive a liquid component from the canister as an aerosol. In order to avoid the depletion of the reactants, the prior art placed individual tabs of reactants in a plurality of sealed pouches. Over time, the pouches would sequentially dissolve and cause a new reaction to generate additional gas for producing the aerosol. However, this technology would be severely inadequate for use in infusion. Large fluctuations of the pressure inside the canister has been found to render these inventions unsuitable for infusion.

It would therefore be advantageous to have a liquid delivery unit, particularly one for dispensing medications, that can be prepared for use and thereafter have a long storage life without pressurization. In this way, there would be little or no tendency for leakage of the medication or other liquid or loss of pressure potential. It would be additionally advantageous to provide a means for quickly and easily creating a gas propellant which would cause the liquid to be delivered in a controlled manner when and as needed.

SUMMARY OF THE INVENTION

The invention herein is a device which is uniquely suited to meet the requirements of hospitals and other institutions. These organizations need to have products which can retain liquids such as medications in usable form over an extended shelf life without leakage or loss of ability to be rapidly and thoroughly dispensed, and which can be activated for such dispensing quickly and without the need for additional equipment (such as pressurized gas cylinders) to effect the activation. Unlike prior art devices, which had to be activated initially (and then suffer short shelf life) or which required complicated and time consuming methods of subsequent activation, the present device remains inert and ready for use for long periods and then can be quickly and easily activated whenever needed.

In accordance with a first aspect of the present invention, there is provided a controllable liquid delivery device comprising a hollow casing having a fluid impermeable wall, an inner surface of the wall surrounding and forming an open interior of the casing, a flexible fluid impermeable membrane disposed within the interior and separating a liquid chamber from a propellant chamber, a liquid filling the liquid chamber, an outlet port through the wall providing fluid communication between the liquid chamber and the exterior of the casing, first and second chemicals separately disposed in the propellant chamber, the first and second chemicals reactive with each other such that upon contact the first and second chemicals react to generate a quantity of propellant gas, means for controlling the rate at which the first and second chemicals generate the propellant gas, barrier means initially separating the chemicals, and means operable to allow one of the chemicals to pass through the barrier means and come into contact with the other of the chemicals, whereby, upon activation of the contacting means, the first and second chemicals react to generate the propellant gas, the propellant gas thereupon expanding against the membrane and causing the membrane to move against the liquid, causing the expulsion of the liquid from the liquid chamber.

In a preferred embodiment of the device, the casing comprises a pair of shells of substantially equal volume and shape which are sealingly joined through the respective bases thereof to form the casing. In another embodiment, a peripheral edge portion of the membrane is retained between the bases of the shells. In yet another embodiment, each shell has a radially disposed flange extending from the base, the flanges cooperating to form the sealable joint between the shells. In another embodiment, the peripheral edge portion of the membrane is retained between the flanges of the bases of the shells. In still another embodiment, the membrane has a surface area of at least about one-half the surface area of the interior of the casing. In another embodiment, the membrane, prior to the reaction of the first and second chemicals, is disposed substantially within the propellant chamber. In another embodiment, the membrane, following substantially complete reaction of the chemicals, is disposed substantially within the liquid chamber.

In still another embodiment, the first chemical is in liquid form. In another embodiment, the second chemical is in liquid form. In another embodiment, the second chemical is in solid form. One of the chemicals is preferably selected from the group consisting of carbonates and bicarbonates, preferably, Group I and II metal carbonates and bicarbonates, even more preferably, sodium bicarbonate, sodium carbonate and calcium carbonate. In a preferred embodiment, one of the chemicals is selected from the group consisting of acids, acid anhydrides, and acid salts, such as, citric acid, acetic anhydride, and sodium bisulfate. Preferably, the first chemical is a citric acid solution and the second chemical is sodium carbonate. In this embodiment, the sodium carbonate is preferably in solid form.

In a preferred embodiment, the barrier means comprises a container in which the citric acid solution is contained and breaching the container permits the citric acid solution to come into contact with the sodium carbonate.

In another preferred embodiment, the controlling means comprises a third chemical moiety that slows the reaction between the first and second chemicals. In another embodiment, the controlling means comprises a physical barrier acting to limit the contact between the first and second chemicals, thereby slowing their reaction. In another embodiment, the controlling function is accomplished by a relief valve in fluid communication with the propellant chamber adapted for allowing for the escape of gas when a pressure generated by the reaction between the first and second chemical exceeds a predetermined level. In a highly preferred embodiment, a combination of third chemicals, geometric configurations, and a relief valve are used to accomplish the control function.

In accordance with another aspect of the present invention, there is provided a method to deliver a liquid from a container which comprises providing a hollow casing having a fluid impermeable wall, a flexible fluid impermeable membrane disposed within the interior of the hollow casing and dividing the interior into a propellant chamber and a liquid chamber containing a liquid, an outlet port through the wall providing fluid communication between the liquid chamber and the exterior of the casing, first and second chemicals disposed in the propellant chamber, the first and second chemicals reactive with each other upon contact to form a quantity of propellant gas, means for controlling the rate at which the first and second chemicals generate the propellant gas, barrier means initially separating the chemicals, means operable to allow one of the chemicals to pass through the barrier means and come into contact with the other of the chemicals, activating the contact means and causing the first and second chemicals to come into contact and react to form the propellant gas, and causing the propellant gas to expand against the membrane and cause the membrane to move and enlarge the volume of the propellant chamber, decrease the volume of the liquid chamber, and expel the liquid contained in the liquid chamber from the liquid chamber through the outlet port.

In the method, the casing preferably comprises a pair of shells of substantially equal volume and shape which are sealingly joined through the respective bases thereof to form the casing. In another embodiment, a peripheral edge portion of the membrane is retained between the bases of the shells. In another embodiment, each shell has a radially disposed flange extending from the base, the flanges cooperating to form the sealable joint between the shells. In another embodiment, the peripheral edge portion of the membrane is retained between the flanges of the bases of the shells. In another embodiment, the membrane has a surface area of at least about one-half the surface area of the interior of the casing. In another embodiment, the membrane, prior to the reaction of the first and second chemicals, is disposed substantially within the propellant chamber. In another embodiment, the membrane, following substantially complete reaction of the chemicals, is disposed substantially within the liquid chamber.

In a preferred embodiment, the first chemical is in liquid form. In another preferred embodiment, the second chemical is in liquid form. In another highly preferred embodiment, the second chemical is in solid form. Preferably, one of the chemicals is selected from the group consisting of carbonates and bicarbonates, particularly, Group I and II metal carbonates and bicarbonates, and sodium bicarbonate, sodium carbonate and calcium carbonate are highly preferred. In a preferred embodiment, one of the chemicals is selected from the group consisting of acids, acid anhydrides and acid salts, preferably, citric acid, acetic anhydride and sodium bisulfate. In a highly preferred embodiment, the first chemical is a citric acid solution and the second chemical is sodium carbonate. In this embodiment, the sodium carbonate is in solid form.

In another embodiment, the barrier means comprises a container in which the citric acid solution is contained and breaching the container permits the citric acid solution to come into contact with the sodium carbonate.

In another embodiment, the controlling means comprises a third chemical moiety that slows the reaction between the first and second chemicals. In another embodiment, the controlling means comprises a physical barrier acting to limit the contact between the first and second chemicals, thereby slowing their reaction.

In accordance with another aspect of the present invention, there is provided a method to generate gas for the controlled delivery of a liquid from a container, comprising separately providing a first and a second chemical, at least one of the chemicals enclosed in a first container, the first and second chemicals being reactive to generate a gas upon contact therebetween, providing means for controlling the reaction rate between the first and second chemicals, and means operable to allow the chemicals to come into contact with one another, activating the contact means so that the first and second chemicals come into contact and react to generate a gas, the controlling means acting to regulate the reaction between the first and second chemical such that the rate at which the gas is generated is substantially linear, and communicating the gas to means operative to drive a liquid from a second container.

In a preferred embodiment, the controlling means is accomplished through the geometric shape of one of the first or second chemicals. In another embodiment, the controlling means is accomplished through the addition of a substantially nonreactive filler. In another embodiment, the controlling means is accomplished through selectively blocking one of the first and second chemicals from reaction with the other of the first and second chemicals. In another embodiment, the controlling means is accomplished through use of a relief valve.

In accordance with another aspect of the present invention, there is provided an apparatus for the generation of a gas for use in a gas driven pump, comprising a first container that is adapted to be situated in fluid communication with the pump, the first container being adapted to separately contain a first and a second chemical as chemical reactants, the first and second chemicals being reactive upon mixing to generate a gas, such that when the first and second chemical are mixed and a gas is generated in the reaction thereof, the apparatus further comprising means for allowing the gas to be communicated from the first container to the pump while the chemical reactants remain in the container.

In a preferred embodiment, the means comprise hydrophobic containment means. In such embodiment, the hydrophobic containment means is preferably a polymeric material, and is advantageously a polypropylene material. Preferably, the hydrophobic containment means is a membrane selected from the group consisting of Tyvek®, Versapel®, Goretex®, Celguard 2400™, Porex®, and BMF™.

In a preferred embodiment, the first chemical is provided as a solution or liquid and the apparatus further comprises a rupturable membrane surrounding the first chemical, such that when the rupturable membrane is ruptured, the first chemical is released and mixes with the second chemical. In another embodiment, the first chemical is provided as a solution or liquid and the apparatus further comprises a rupturable membrane surrounding the second chemical, such that when the rupturable membrane is ruptured, the second chemical is released and mixes with the first chemical. In another embodiment, the hydrophobic containment means is a membrane forming a first pouch, the first pouch forming a second pouch surrounding the first chemical and a third pouch surrounding the second chemical and further comprising means therebetween that is adapted to be opened to allow the first and second chemical to mix. In another embodiment, the first pouch further comprises an internal wall and the second and third pouch are formed by reversibly closing the internal wall of the first pouch upon itself. In another embodiment, the internal wall of the membrane is closed by twisting the first pouch and the first and second chemical are allowed to mix by untwisting the membrane.

In accordance with another aspect of the present invention, there is provided a method to generate gas for the controlled delivery of a liquid from a container, comprising separately providing a first and a second chemical, at least one of the chemicals enclosed in a first container, the first and second chemicals being reactive to generate a gas upon contact therebetween, providing means for controlling the reaction rate between the first and second chemicals, and means operable to allow the chemicals to come into contact with one another, activating the contact means so that the first and second chemicals come into contact and react to generate a gas, the controlling means acting to regulate the reaction between the first and second chemical such that upon attainment of a predetermined pressure within the first container, the container is maintained at the predetermined pressure, and communicating the gas to means operative to drive a liquid from a second container at a substantially linear flow rate.

In a preferred embodiment, the controlling means is accomplished through use of a pressure relief valve.

DETAILED DESCRIPTION OF THE PREFERRED EMBODIMENTS

We have surprisingly discovered that it is possible to make a device that provides controlled liquid delivery over time that can be prepared for use and thereafter have a long storage life without pressurization. In this way, there is very little tendency for leakage of the medication or other liquid or loss of the unit's pressure potential. The device in accordance with the present invention additionally provides a means for quickly and easily creating a gas propellant that causes the liquid to be delivered in a controlled manner when, and as, needed.

The basic aspects of the invention that obtain these aforementioned advantages arise from the use of a controlled chemical reaction that evolves gas. The chemical reaction is started by an operator of the device, when needed. The gas evolution reaction occurs in a container and the gas evolved operates to apply pressure on a liquid separated from the gas evolution reaction. It is preferable, indeed arguably necessary, that the gas evolution reaction be separated from the liquid to be infused into a patient, since, often the chemicals used in the gas evolution reaction or the byproducts from the reaction are toxic and/or undesirable for administration to a patient. In either case, it will be understood that the pressure exerted on the liquid will force the liquid out of a port at a flow rate that is proportional to the rate of the gas evolution reaction.

Figure 1:
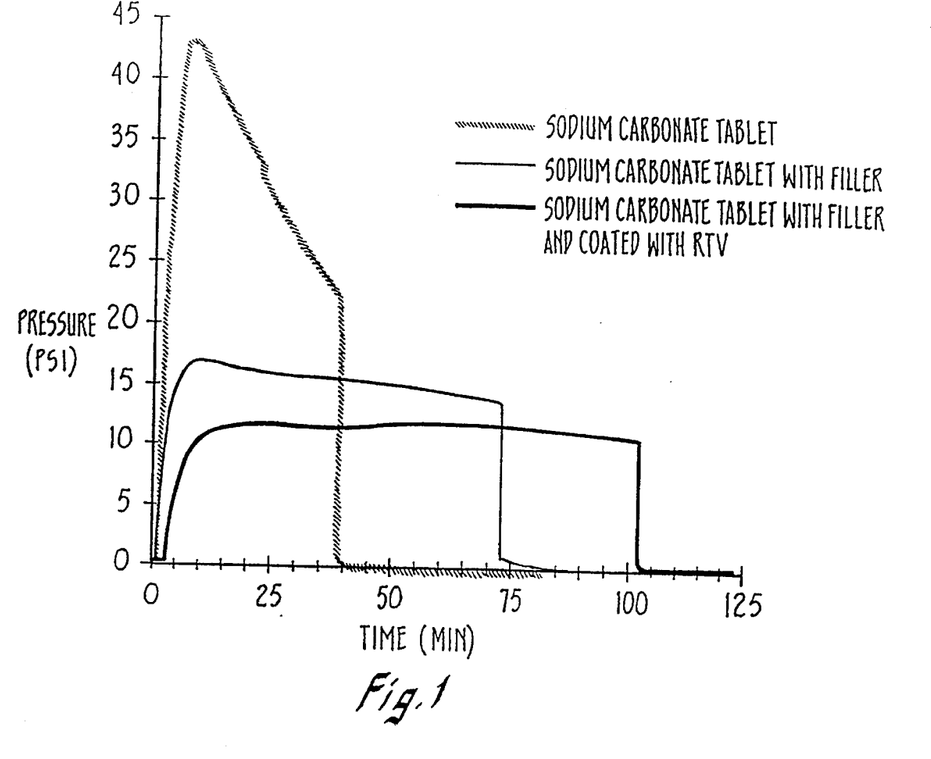
FIG. 1 is a graph showing the pressure developed over time in three different reactions of sodium carbonate ($Na_2CO_3$) and citric acid ($C_6H_8O_7$; 2-hydroxy-1,2,3-propanetricarboxylic acid): (i) pelletized sodium carbonate, (ii) pelletized sodium carbonate bound with a filler, and (iii) pelletized sodium carbonate bound with a filler and covered with a room temperature vulcanizing (RTV) silicone adhesive sealant on the top and the bottom of the pellet.

Referring now to FIG. 1, there is provided a graph showing the pressure developed over time in three different reactions of sodium carbonate ($Na_2CO_4$) and citric acid ($C_6H_8O_7$; 2-hydroxy-1,2,3-propanetricarboxylic acid): (i) pelletized sodium carbonate, (ii) pelletized sodium carbonate bound with a filler, and (iii) pelletized sodium carbonate bound with a filler and strips covered with a room temperature-vulcanizing (RTV) silicone adhesive sealant.

Figure 2A:
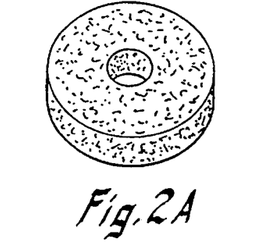
FIGS. 2A and 2B illustrate two embodiments of the solid reactant of the present invention.
Figure 2B:
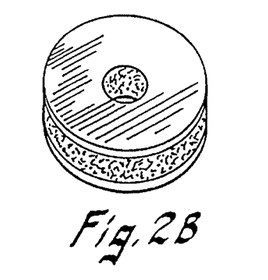

In each of the reactions, a solution of citric acid (7.5 gm/15 ml (2.6M)) was reacted with 2.72 grams (0.025M) of sodium carbonate. Also, in each the sodium carbonate was formed into a "donut shaped" pellet (as shown in FIG. 2a) using a tablet or pill press. In reaction (ii), prior to making the pellet, 15% by weight of a filler, polyvinylpyrrolidone (PLASDONE, available from ISP Technologies, Inc., Wayne, N.J.), was added to the sodium carbonate. In reaction (iii), a similar pellet to that made for reaction (ii) was prepared containing the sodium carbonate and 15% by weight of the polyvinylpyrrolidone. This pellet was of the same geometry as that used in reactions (i) and (ii), however, a room temperature vulcanizing (RTV) silicone adhesive was applied to the top and bottom of the pellet, as shown in FIG. 2b, so as to reduce the surface area of the sodium carbonate and filler that would be exposed to the citric acid solution. In this particular reaction, the RTV was PERMATEX®, available from Loctite Corporation, Cleaveland, Ohio (Part No. 66B).

In order to run the reactions, a sealable container was used which allowed for the displacement of a liquid therefrom. The container is made up of a first container which encloses a liquid. Also contained in the container is a second container that holds the citric acid solution. Thus, when the pellets are immersed in the citric acid solution in the second container, the liquid in the first container will be displaced and its flow rate and pressure over time can be measured.

Even in this very rudimentary test, it will be appreciated that without the use of a controlling agent (i.e., in reaction (i) where the sodium carbonate is reacted neat with the citric acid solution), liquid is forced out at too rapid a rate in the early stage of the reaction to act effectively in an infusion pump. Then, the reaction slows down and flow rates become very slow. An infusion pump must provide a relatively constant flow rate over time. This is not achieved where the reactants are reacted neat.

The use of a controlling agent, configurations, and/or controlling mechanisms, on the other hand, can be used to flatten the curve of flow rate or pressure generated over time, as seen in the results from reactions (ii) and (iii).

The present invention contemplates the use of a variety of controlling agents. Virtually any material, geometry, or enclosure that acts to limit the contact between two reactants can act as a controlling agent for the purposes of the present invention. For example, as mentioned, fillers are quite effective, such as polyvinylpyrrolidone (i.e., Plasdone, mentioned above), polyethylene glycol (i.e., PEG 400 available from Olin Corp., Stamford, Conn.), and polyvinyl alcohol (i.e., PVA 205S available from Air Products, Allentown, Pa.). Similarly, there are a large number of excipients or carriers that will act to slow the chemical reaction.

Further, a variety of geometries or enclosures can also be used that limit the rate at which gas is generated from the reaction. For instance, a reactant can be partially enclosed in a completely or partially insoluble material, such that only a limited surface area of one reactant is available for reaction. This is accomplished in a preferred embodiment through the use of the RTV agent, however, it will be understood that other insoluble materials, such as waxes, metal tubes, and other materials can also be used with similar success.

Moreover, it will now be appreciated that the reaction rates of the chemical moieties can be tailored to meet a user's specific requirements. In other words, through arranging or allowing contact of the chemicals in a predetermined manner, a pressure profile can be generated. The pressure profile can, for example, start at an initial profile designed to deliver florid from the pump at an initial slow rate and can, thereafter, increase, to deliver fluid at a second increased rate. This is advantageous in certain applications, such as delivery of cancer chemotherapeutic agents. Multiple stages of fluid delivery can be implemented through predetermination of a desired pressure profile and design of the chemical reactants' configurations or contact to achieve that profile.

In simple embodiments, it will also be appreciated that it is possible through use of the present invention to make pumps that allow for the delivery of a variety of predetermined, constant flow rates. Pumps prepared in accordance with the present invention can be prepared to generate flow rates from as low or lower than 2 ml. per hour to upwards of 200 ml. per hour. Particularly preferred flow rates are in the range of from about 5, 10, 15, 20, 50, 100, 150, or 200 ml. per hour. Therefore, a pump can be prepared with sufficient chemical reactants to allow only a fluid flow rate of 5 or 10 ml. per hour. Or, the pumps can be similarly prepared to provide a flow rate of 15 or 20 ml. per hour.

The specific quantities of reactants necessary to achieve desired flow rates will depend on the particular choice of the reactants and the pressure and/or flow rate profile desired. Such quantities will be determinable empirically by one of ordinary skill in the art in light of the present specification and without undue experimentation.

With this background on the mechanisms used to controllably generate a gas in accordance with the present invention, we shall now turn to a discussion of the apparatus that can be used to contain the gas generation reactants and the liquid to be delivered, in such a manner that when the reaction is commenced, the liquid can be pumped from the apparatus to the patient in a controlled, safe, and sterile manner.

Figure 3:
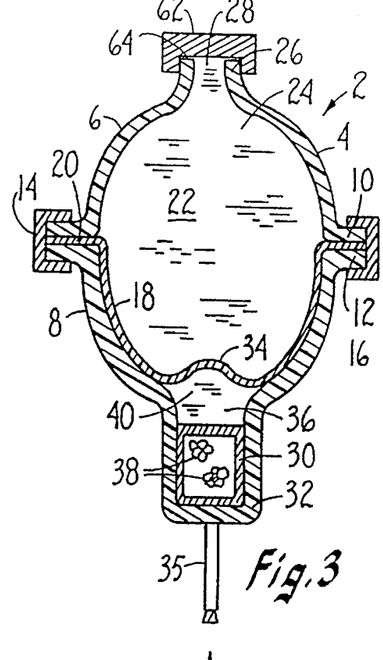
FIGS. 3 through 6 are a series of cross-sectional drawings of the device, showing its initial condition and condition at steps during pressurization and dispensing of the contained liquid.

One such device that fulfills the above objectives of the present invention can be understood by reference to the drawings, with initial reference to FIG. 3. The device 2, preferably is formed of a casing 4. The casing 4, can be formed of any suitable material and can be rigid, flexible, or otherwise, and may even be a substantially flexible material, such as in the case of materials used to manufacture IV bags. It will be appreciated that it is preferred to prepare the casing 4 of a substantially rigid material, because, there is less chance that the casing would rupture or unattractively expand and have increased durability. However, substantially flexible materials would nevertheless function equivalently. Moreover, such materials could advantageously be disposed within another outer casing to provide support and reduce concerns about rupture, expansion, or durability.

Figure 11:
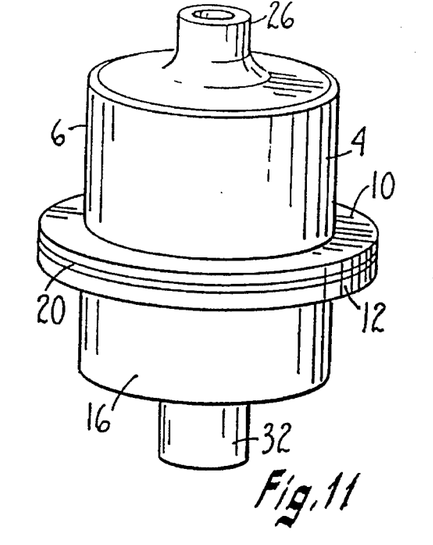
FIGS. 11 and 12 are respectively a perspective view and a cross-sectional side elevation view of an alternative embodiment of the device of this invention.
Figure 12:
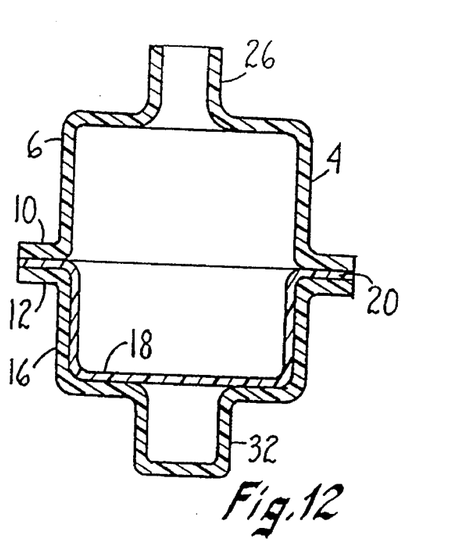
Figure 13:
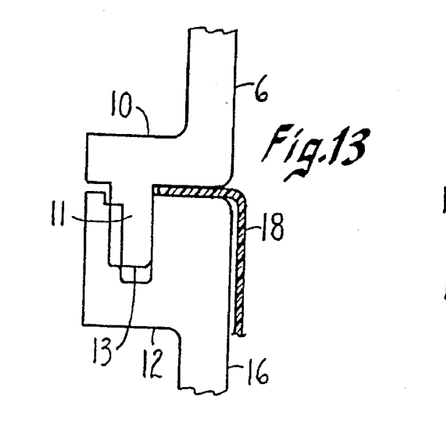
FIGS. 13 and 14 are cross-sectional views of a portion of the device illustrating alternative means for joining the two halves of the device and securing the membrane.
Figure 16:
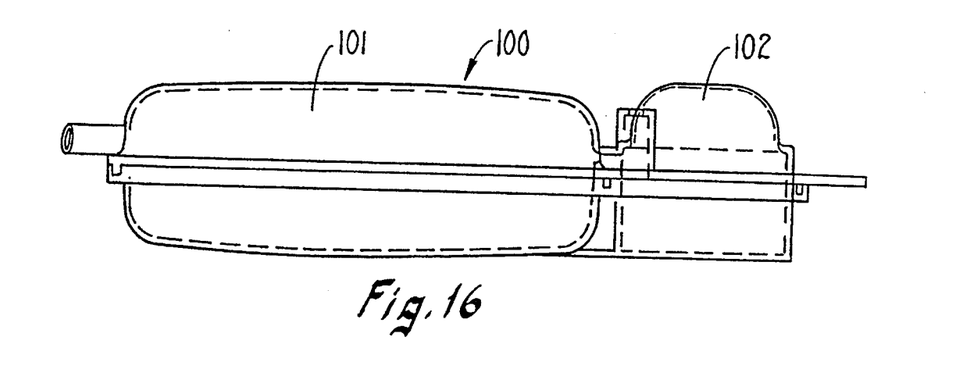
FIGS. 16 and 17 are respectively the sectional side elevation view and the sectional top plan view, each sectioned along its mid-line, of another embodiment of the device of this invention.
Figure 17:
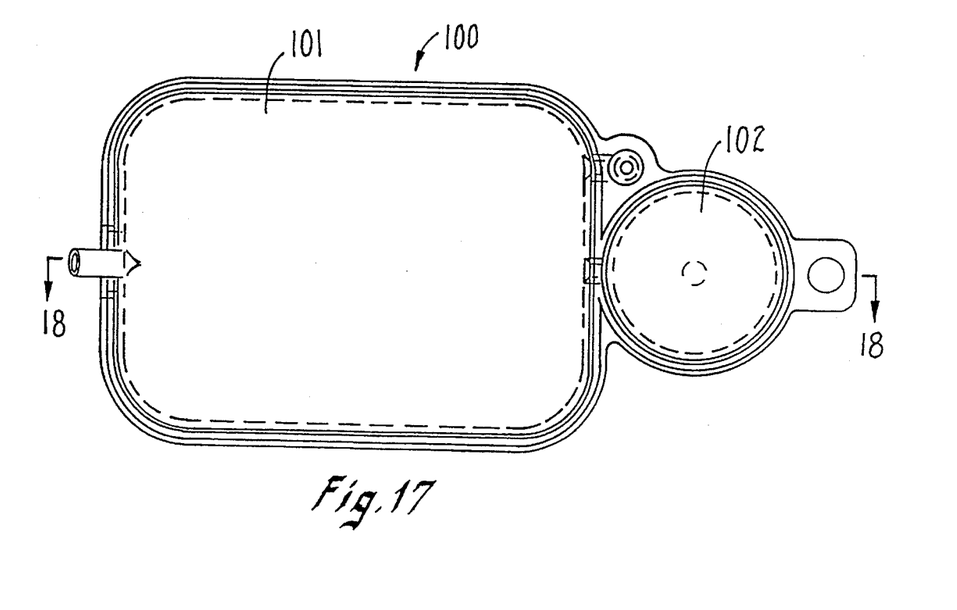

In the embodiment pictured in FIG. 3, however, the casing 4 is prepared from a substantially rigid material and is conveniently formed in two halves 6 and 8. Any convenient shape of the casing 4 may be used, such as approximately spherical (so that halves 6 and 8 are essentially hemispheres) as shown in FIGS. 3–6, cylindrical with rounded edges (as shown in FIGS. 11–13), or a generally rectangular or cube shape with rounded edges and corners (as shown in FIGS. 16–17) as long as the shape is such that substantially all of the contained liquid will be dispensed and little or none will remain in the container after use, and that the desired external shape of the device can be maintained when the device is pressurized.

(For brevity herein, reference to casing 4 shall include both halves 6 and 8 when the subject discussed is equally applicable to the entire casing 4. When individual halves 6 and 8 are to be discussed, they will identified separately. In any event the context will make it clear to the reader skilled in the art which reference is intended.)

Halves 6 and 8 are normally of equal or substantially equal shape and volume. Forming the halves of significantly different shapes or volumes is to be avoided since the movement of membrane 18 and the efficient dispensing of the contained liquid will be hampered or prevented by such substantially unequal shapes or volumes. The membrane 18 is a flexible member that is essentially distended into the lower half 8 when filled by the liquid and becomes extended into the upper half 6 when the gas generating reaction forces liquid through the neck 28 of the device 2. Thus, the distension and extension of membrane 18 must not be hampered so that liquid can be delivered from the device to the patient. As will be appreciated, this function can be fulfilled by a variety of materials and structures, as will be discussed in greater detail below.

Figure 14:
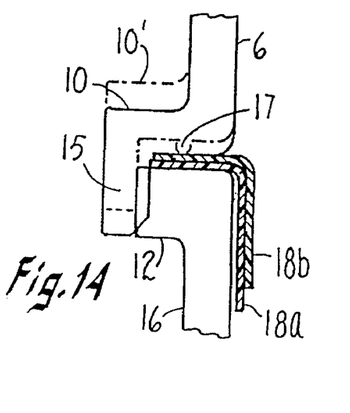

The halves 6 and 8 are joined at their adjoining peripheries by any convenient sealing means. In FIGS. 3–6 and 11–12, the sealing means are opposed radial flanges 10 and 12, which in turn are locked together by an annular channel 14 (not shown in FIGS. 11–12). In FIGS. 13 and 14, alternatives are shown in which a projection on the face of one flange interfits or overlaps with a corresponding member on the face of the other flange, with the membrane being secured between the two faces. Preferably the projection and the corresponding member are continuous around the faces of the flanges. For instance, there may be an annular ring-and-groove structure as in FIG. 13, in which an annular ring 11 projects from the face of flange 10 and fits into a corresponding annular groove 13 in flange 12, or there may be a peripheral male-female fit as shown in FIG. 14, in which an annular lip 15 projects from the peripheral edge of flange 10 and extends outwardly over the outer periphery of flange 12. Annular ribs 17 (shown in the phantom view of the pre-compression position of flange 10 in FIG. 14) help retain the membrane in place and enhance the sealing effect of the flanges so that no fluid escapes or depressurization occurs through the joint between the flanges.

Figure 6:
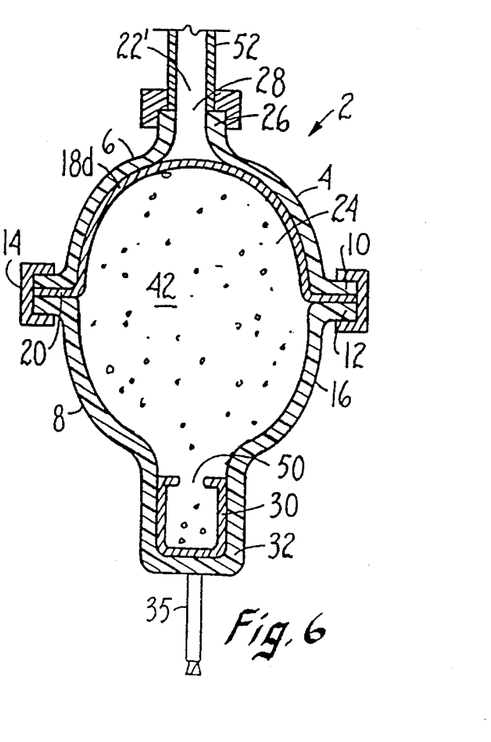
Figure 7:
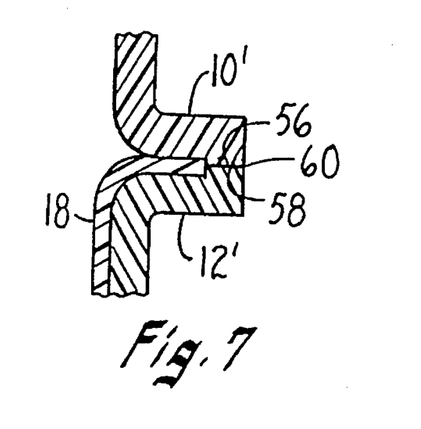
FIG. 7 is a cross-sectional detailed view illustrating an alternative form of construction of a portion of the device.

The flanges may be joined in any convenient sealing manner. The sealing means may if desired be releasable, so that the device can be reused, by being disassembled and sterilized (with if desired replacement of the membrane) and then reassembled and refilled with a new liquid and new propellant chemicals. Bolts, clips, or other mechanical fasteners spaced apart around the flanges may be used for releasable sealing. For instance, the embodiment shown in FIGS. 3–6 contains a channel 14 to hold the two halves 6 and 8 together. Alternatively, if releasability is not desired, the halves of the device can be sealed by suitable adhesives applied to the flanges or by mechanical or thermal means such as ultrasonic or thermal welding of the mating surfaces of the flanges. For instance, in the embodiment shown in FIG. 7, flanges 10' and 12' each has a small shoulder (respectively 56 and 58) and their opposed surfaces are closely abutting. Those surfaces can then be joined as by an adhesive 60 or by ultrasonically, thermally, or frictionally welding to form a tight circumferential seal around the casing 4. Adhesive application or ultrasonic or thermal welding may occur only at points A (FIGS. 13 and 14) or the mating structures may be configured to have larger surface areas in contact for adhesion or welding as shown in FIG. 7. Those skilled in the art can readily determine the appropriate manner of sealing for the end use contemplated.

Casing 4 has a relatively thin gas- and liquid-tight wall 16 which for the most part is rigid or semi-rigid. It will be typically be made of of a plastic, polymeric, or hard rubber material, with the particular construction material being selected based upon the materials compatibility with the fluid contained. When liquid medications are to be contained, the casing 4 will be made of a material which can be sterilized (through heat, chemical treatment, or otherwise) and which is inert to the medication.

The casing material may be transparent so that the liquid inside can be viewed, or it may be translucent or opaque. If transparent or translucent, it may also be tinted or otherwise chemically treated to avoid light degradation of the contained liquid. Many suitable materials contain ultraviolet light stabilizers or blockers that can act to protect the liquid contained therein from light degradation. The properties of such materials are widely described in the art and literature; see, e.g., Rubin, *Handbook of Plastic Materials and Technology* (John Wiley & Sons, Inc. (1990)) and Morton "Rubber Technology" (3d ed., Van Nostrand Reinhold Co. (1987)). Those skilled in the art will have no difficulty selecting suitable materials for various embodiments and uses of the device.

Within the casing 4 is a flexible membrane 18 which is also gas- and liquid-tight and is shaped preferably to match the inner contours of wall 16 in either of the halves 6 or 8. As was mentioned above, the membrane essentially distends into the lower half 8 when filled by the liquid and becomes extended into the upper half 6 when the gas generating reaction forces liquid through the neck 28 of the device 2. Thus, the distension and extension of membrane 18 must not be hampered so that liquid can be delivered from the device to the patient.

Figure 15:
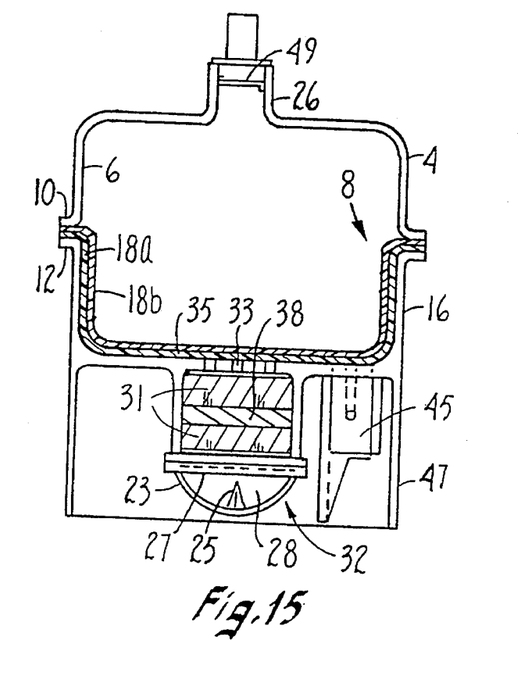
FIG. 15 is a cross-sectional view of another embodiment of the device of this invention, illustrating another embodiment of the chemical container and the presence of an optional relief valve.

The surface area of the membrane 18 will normally be larger than the interior surface area of either of the halves 6 and 8 (or of the larger, if they are of different sizes), since it will also have a peripheral area 20 for retention between the flanges 10 and 12 and preferably will also have some degree of pleating to enhance its ability to move across the device under gas pressure. The membrane may be of a single layer of material as shown in FIGS. 3–7. Preferably, however, there will be two or more layers of material, as shown in FIGS. 14 and 15. Multiple layers provide a significant margin of safety, since a tear or leak in a single-layer membrane permits leakage of liquid, while even if there is a tear or leak in one layer of a multiple-layer membrane the remaining intact layers will safely retain the liquid. Further, since the membrane must have a certain thickness to withstand the gas pressure, a single-layer membrane must be of that overall thickness in the single layer, thus rendering it less flexible than a multi-layer membrane of the same overall thickness, since the thinner individual layers are separately more flexible.

As will be mentioned below, the separate layers of a multi-layer membrane are preferably bonded only at their periphery, so that they can slide freely against each other as the membrane moves under the gas pressure and thus the membrane as a whole can flex easily across the interior of the device in response to the gas pressure.

Membrane 18 can be made of a wide variety of polymeric materials, including various flexible plastics and rubbers. As with the casing materials, the properties of suitable membrane materials are widely described in the art and literature, including the aforementioned Rubin and Morton texts; again no difficulty will be had in selecting a suitable material. It is preferred that the membrane 18, while being flexible, have relatively minimal elasticity, since the membrane is intended to move the liquid through the interior of the casing. If the elasticity is too great, the membrane will stretch irregularly and some of the liquid may become trapped in folds of the stretched membrane.

Initially the membrane 18 is positioned within (or distends into) half 8 as shown in FIG. 3 so that it substantially covers the inner surface of the half. The liquid 22 to be dispensed is contained in a "liquid chamber," i.e., that portion of the interior 24 of the casing 4 which is bounded by the inner surface of wall 16 in half 6 and the corresponding surface of membrane 18 as the latter lies against the inner surface of wall 16 in half 8. Neck 26 is formed in half 6 (preferably at the center of its wall 16). Neck 26 opens to the outlet port 28 through which the liquid 22 is dispensed, as will be described below. If desired, there may be a one-way valve 49 in neck 26 (FIG. 15) to prevent loss of any liquid 22 even if the outlet port 28 is not capped. The one-way valve 49 would be opened by pushing tubing or a similar object through the neck 26, in a similar manner to that shown in FIG. 8B.

Figure 10:
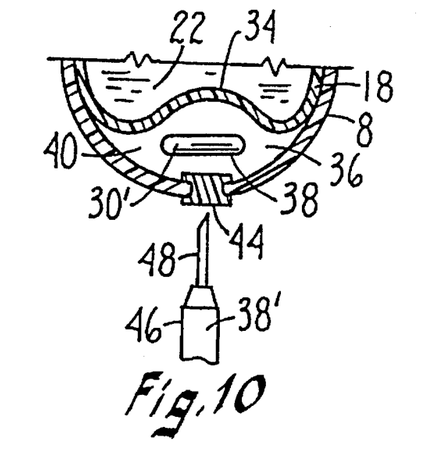
FIG. 10 is a partial cross-sectional view showing an alternative embodiment of the chemical container.

The device will contain some form of barrier to initially separate the two reactive chemicals. In the embodiment shown in FIGS. 3–6, the barrier is in the form of an openable gas- and liquid-tight container 30. Container 30 may, but need not, be positioned diametrically opposite from outlet port 28. In FIGS. 3–6 the container 30 is shown as positioned in a well 32 which is formed in the wall 16 of half 8. Alternatively, however, container 30 may be completely within half 8 as indicated in FIG. 10 at 30'. This latter configuration is less preferred, however, since it makes it more difficult to open the container 30, as will be described below.

Membrane 18 is positioned between liquid 22 and container 30, and the space within the interior of the casing on the side of membrane 18 opposite to liquid 22 comprises a "propellant chamber" into which the propellant gas will be evolved as described below. If desired, there may be a small depression 34 formed near the midpoint of membrane 18 as indicated in FIG. 3, the purpose of which will be described hereafter. Membrane 38 and part of the wall 16 of half 8 cooperate to form a chamber 36. Container 30 may be either in chamber 36 or immediately adjoining it, as shown in FIGS. 3 and 10.

The driving force for the expulsion of liquid 22 from the interior 24 of casing 4 is provided by a volume of gas which is evolved by the reaction of two chemicals, which as noted are kept separate from each other until the time at which the gas formation is desired. Considering the embodiment of FIGS. 3–6, one of the two chemical reactants will be contained initially within container 30. For ease of description herein, the chemical reactant contained in container 30 will sometimes be referred as the "first" reactant and the other chemical reactant, initially kept separate from container 30 (or separated within container 30), will be referred to as the "second" reactant. Both chemicals must be substantially inert toward the membrane 18, casing 4 and container 30 and stable throughout the entire expected shelf life and service life of the product. They will, however, be readily and controllably reactive with each other under ambient conditions, preferably simply upon contact.

In a preferred embodiment, one of the reactants will be a carbonate or bicarbonate compound, particularly preferred being $Na_2CO_3$ (known as soda ash in some of its commercial forms) and $CaCO_3$; compounds like $NaHCO_3$ may also be used but one must be careful to keep them below the temperature at which they exhibit significant decomposition (such as $NaHCO_3$, which begins to evolve $CO_2$ gas at temperatures above about 45° C.). In the same preferred embodiment, the other reactant is preferably an inorganic acid, an acid anhydride, or an acid salt. Typical preferred examples of each are citric acid, acetic acid anhydride, and sodium bisulfate. Stronger acids such as HCl or $HNO_3$ or weaker acids such as acetic acid may also be used.

The most preferred combination is considered to be sodium carbonate and citric acid, both of which are quite stable but which react to evolve $CO_2$ gas upon contact. In most cases, it will not matter which is considered the first reactant and which is considered the second reactant. Generally, however, as will be appreciated, one of the reactants will be a liquid (or in solution), and the other reactant, either as a solid, liquid, or in solution. This helps to ensure that the two reactants can mix and react, Either one chemical itself may be a liquid or one of the chemicals may be dissolved or dispersed in a liquid carrier or solvent, preferably water. In a preferred embodiment, a citric acid solution and a solid sodium carbonate are used for the gas generation. Therefore, those skilled in the art can readily select and designate the particular materials to be used depending on ease of handling, speed of reaction, inertness toward the other materials of the system and so on. However, as was discussed above, a critical aspect of the present invention is the controllable release of gas. In FIG. 1, the superiority, in terms of almost linear liquid delivery is seen when a control agent is incorporated with one of the reactants.

It is preferred that the two reactants fully react with each other on contact, however, where the reactants are relatively slow in reacting or in generating gas, it is also possible to include a catalyst (as a third component) to promote or accelerate the reaction. This is less preferred, however, since it complicates the system and adds to the cost. Initially such catalyst will be disposed separately with one or the other of the reactants, with the disposition chosen to minimize any potential for the catalyst to react prematurely with the single reactant it is in contact with.

In a preferred embodiment, the system comprises a liquid reactant and a solid reactant. The liquid reactant 40 will normally be retained in the chamber 36. The reactant 38 in chamber 30 may either be in liquid form or in dry form, and usually is in the form of dry powder, granules or one or more porous pellets to provide an extended surface area to increase the rate of contact and reaction.

There are several types of barriers which can be used to separate the chemicals 38 and 40 until the device is to be used, but which can be breached to permit the chemicals to mix to generate the gas 42. Where the barrier is in the form of container 30, it may be made of a breakable material, such as thin glass or thin brittle plastic, which can be easily broken to allow the chemicals to mix. For instance, if the casing material in the area of well 30 has some degree of flexibility and the container 30 is sized to abut the inner wall of well 32 as shown in FIG. 3, a modest squeezing of the outside of the well 32 by simple finger pressure will cause the container 30 to fracture and allow the chemicals to mix.

In the alternate configuration shown in FIG. 10, where there is no well 32 and the container 30' is within chamber 36, a small rubber self-sealing membrane or grommet 44 is mounted through the wall 16 of half 8 so that a long sharp object such as a needle can be inserted through grommet 44 to contact and fracture container 30'.

Yet another embodiment is shown in FIG. 15, in which the bottom of dell 32 is in the form of a flexible cap or dome 23 with a spike or similar piercing device 25 mounted on its inside. The barrier is in the form of a perforable membrane 27 which is mounted across the base of the dome portion 23 of the well 32, to form a liquid-tight chamber 29 under the dome, with the liquid chemical 40 initially retained in the chamber 29 and isolated from the other chemical 38 which is positioned in the remaining portion of the well 32. When the flexible dome 23 is depressed by the user's fingers, the spike 25 penetrates and perforates the membrane 27 and the liquid chemical 40 flows into the rest of well 32 and contacts the other chemical 38 (here shown in a pellet form) in container 30, causing the gas-generation reaction. If desired, porous sponges or similar liquid retaining and dispersing means 31 may be used to cause the liquid chemical 40 to flow throughout the container 30 in a controlled and directed manner. A screen or perforated plate 35 having openings 33 may be used to retain the solid materials in container 30 but allow the evolved gas 42 to pass freely out of the well 32 and into contact with membrane 18.

In yet another embodiment also indicated in FIG. 10, one may dispense with a container and have the first chemical 38 contained in a separate syringe 46, the needle 48 of which can be inserted through the barrier 44 (in the form of a membrane or grommet) so that the liquid chemical 40 can be injected into the other chemical 38 within the chamber 36. This configuration is not preferred, however, because it requires two separate components (albeit that they may be kept together as a single package). In addition, it is much less rapid to use than simply having a breakable container 30 such as in FIG. 3.

As will be evident from FIGS. 15–17, that portion of the propellant chamber 36 in which the chemicals are initially housed may be spaced adjacent to or spaced apart from the portion which is adjacent to the membrane 18 and into which the gas evolves. In such case the two portions (designated 36a and 36b) will be connected by a conduit 51 for the gas to pass from the reacting chemicals into contact with membrane 18. The conduit may be in a tube form as shown in FIGS. 16 and 17, or it may simply be a screened opening as shown in FIG. 15.

Hook or hole 35 may be provided to enable the device 2 to be hung from a hospital pole or similar suspending hook. If a hook 35 is used with the configuration shown in FIG. 10, membrane 44 will have to be positioned so as not to interfere with the hook 35.

The device may also have an exterior rigid skirt 47 to allow it to be placed in standing position on a shelf for storage, and to protect the well 32 or dome 23 from accidental contacts which would cause the barrier 27 to be breached and the device inadvertently activated and to protect relief valve 45 (if present) from damage.

Figure 4:
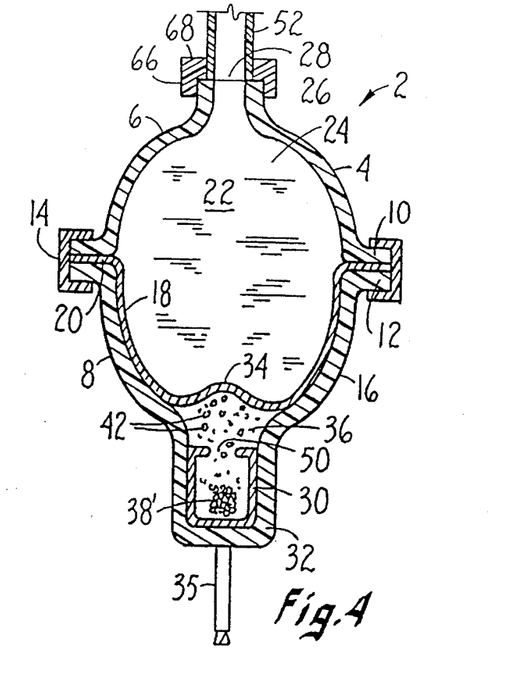
Figure 5:
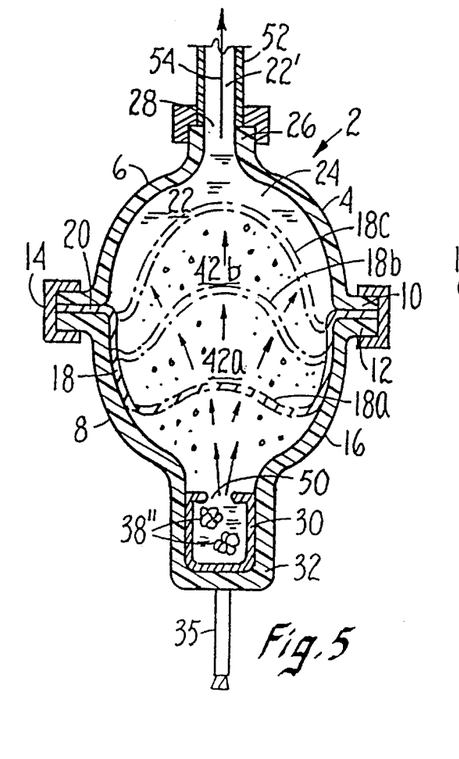

The operation of the device will be evident from the FIGS. The barrier (e.g., container 30 or a membrane (not pictured)) is first breached so that the liquid chemical 40 quickly flows into the interior of container 30, contacting chemical 38 and reacting as indicated at 38'. As noted above, the breaching may be by breakage of container 30, as illustrated in FIGS. 4–6, so that the liquid chemical 40 flows into the fractured container 30 via openings 50. Alternatively, as shown in FIG. 13, breaching may be by perforation of a membrane between the two chemicals. In the embodiment shown in FIG. 13, pressure on the dome not only causes the membrane to be perforated, but it also causes the liquid chemical 40 to be forced into contact with the other chemical 38, thus augmenting the normal tendency of the chemical 40 to flow of its own accord. This forcing will also be advantageous when the device is mounted with the well in a downward or sideways position where normal flow would be limited or prevented.

The reaction between chemical reactants 38 and 40 results in rapid evolution of gas 42 which initially moves as bubbles through the liquid. At the time of FIG. 4, the reaction of the two chemicals 38 and 40 has just started and there is not yet enough evolved gas 42 to cause the membrane 18 to move. As the gas 42 is evolved it moves through the liquid and begins to concentrate under membrane 18. As more gas is evolved, it causes the membrane 18 to move so that the membrane 18 travel is uniform along the diametrical axis of the casing 4 between the well 32 and the outlet port 28. As noted above, it may be desired to have a depression 34 present in which the gas initially evolved can concentrate, thus causing the middle of the membrane 18 to move first, with the depression 34 essentially leading the movement. Three representative subsequent stages of movement are shown diagrammatically in FIG. 5 with the membrane 18 in each stage indicated as 18a, 18b and 18c respectively. As the gas 42 continues to be evolved and the membrane 18 extends or expands away from casing 8 and into the interior of casing 6 as indicated at 42a and 42b. This movement of the membrane 18 forces the liquid 22 out through the outlet port 28 and outlet tubing 52 as indicated at 22' and by arrow 54. The small amount of liquid which was in chamber 36 remains at the bottom of the device as the reactants continue reacting as indicated at 38".

The conclusion of the dispensing of the liquid 22 from the unit 2 is illustrated in FIG. 6. At this point the reaction between the two reactants 38 and 40 is completed. The entire interior volume of the casing 4 is now filled with the evolved gas 42 and the membrane 18 has moved entirely to the opposite end of the casing 4 within half 6 as indicated at 18d. A small amount of remaining liquid may be contained in the tubing 52 as indicated at 22', and that can be drained or discarded as desired by the user. It will be seen that because of the generally spherical shape of the casing 4, the membrane in position 18d has forced essentially all of the liquid 22 from the casing 4 and that substantially none remains captured in pockets, crevices, corners or other traps. At this point the unit 2 can be disconnected from the tubing 52 and discarded.

Assembly of the device 2 is straightforward. In the embodiment shown in FIGS. 3–6, the container 30 is first filled with the first reactant in liquid or dry form and then sealed. Container 30 is then placed in half 8 (preferably in well 32 if such is present). Thereafter, the second reactant 40 (as or in a liquid) is placed into the bottom of half 8 adjacent container 30 and membrane 18 is laid over the inside surface of half 8 to retain the liquid chemical reactant 40 within the chamber 36 which forms behind the membrane. The depression 34, if present, is normally formed in the membrane 18 either at the time of the membrane manufacture or at the time it is placed into the half 8. Thereafter half 6 is aligned with and placed over half 8, with the ends of the periphery of the membrane 18 compressed between the flanges 10 and 12, and the casing 4 is sterilized, closed, and sealed as indicated in FIGS. 3 or 7. However, it is possible that one could close, seal, and sterilize the device 2. The device 2 is now ready for filling with the medication or other liquid 22.

[In the embodiments shown in FIGS. 13–17, the liquid reactant 40 is first placed in chamber under the dome and the sealing membrane is put into place to contain and isolate the reactant 40. The reactant 38, in either liquid or solid form, is then placed in container 30 (the remainder of well 32) and the device 4 with membrane 18 then assembled and filled with liquid 22 as described in the preceding paragraph.]

Once liquid 22 has been placed into the interior 24 of casing 4, the device 2 can be closed by means of cap 62 placed over the outlet port 28, either used alone or in conjunction with one-way valve. This can be a simple closed cap which is force fitted or threaded onto neck 26 (if threads are present). A liquid seal such as an O-ring or gasket 64 may be present if desired. When it is time to use the device 2, cap 62 is removed and a female fitting 66 having an opening 68 in which tubing 52 is mounted is attached to neck 26 in place of cap 62. The device 2 is then ready for rupturing of the container 30 and dispensing of the liquid 22.

Figure 8A:
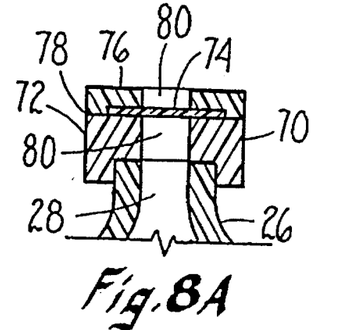
FIGS. 8A and 8B show, respectively, an embodiment of a cap for the/device and such cap in use with a liquid distribution tube.
Figure 8B:
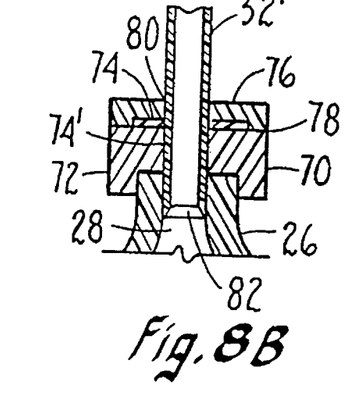

In another embodiment, as shown in FIGS. 8A and 8B, cap 62 is replaced by a cap 70 formed of three pieces: a base 72, a rupturable membrane 74 and a outer annulus 76. The membrane 74 should be mounted under tension and made of a material with a significant degree of elasticity. The base 72 and the annulus 76 are sealed together at 78 to trap membrane 74 between the two. Both the annulus 76 and base 72 have a central hole 80 aligned with the outlet port 28. However, the membrane 74 is solid across the hole 80 and seals the device 2 against loss of liquid 22 or contamination from the environment When it is desired to use the device 2, a piece of rigid tubing 52' is thrust into hole 80 to puncture membrane 74 and gain access to outlet port 28. If desired, the forward end of tubing 52 may be beveled as shown at 82 to form a cutting edge and facilitate puncturing of membrane 74. When punctured membrane 74, being elastic and under tension, will substantially retract out of the interior of neck 26, minimizing any tendency of the membrane material to interfere with the interference fit of tubing 52' in hole 80. The rigid portion of the tubing 52' can be just an end portion of the overall tubing 52 or it can be a separate coupling into which a flexible section of tubing 52' is added at the outward end (not shown).

Other means of capping and sealing the unit will be immediately apparent to those skilled in the art.

Also present may be exhaust or relief valve 45. This valve permits venting of the gas in the interior of the device should the pressure get too high for optimum flow of the dispensed liquid. It may also be used to vent the remaining gas 42 after the device has been emptied of liquid 22.

Figure 9:
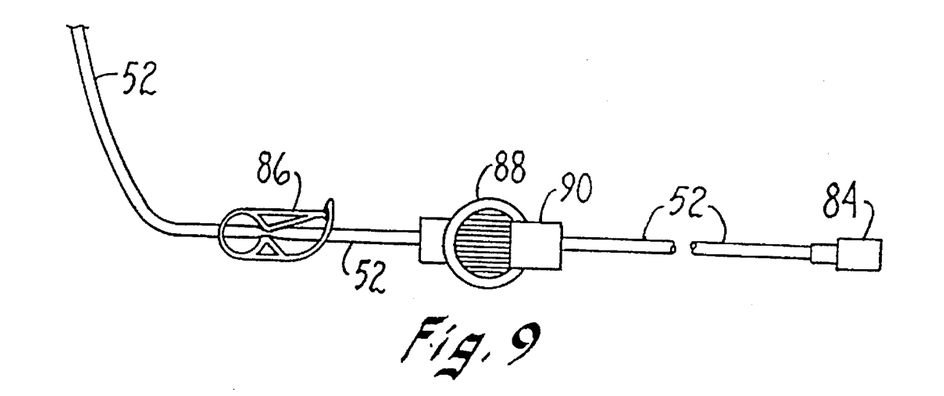
FIG. 9 illustrates typical components in the fluid outflow line for controlling flow and filtering the liquid.

A further control mechanism for dispensing a liquid 22 through the tubing 52 is shown in FIG. 9. The tubing 52 communicates with a patient intravenous apparatus or other dispersing apparatus through a coupler 84. The coupler 84 may be a male luer lock adapter that closes the line 52 when the coupler 84 is disconnected from the patient or other dispersing apparatus, if it is desired to retain some of the liquid for further and subsequent dispersing (in which case the membrane 18 will be held at some intermediate position such as 18a, 18b or 18c until the system is again connected to the patient or further dispensing apparatus and the fluid flows from the system). The luer lock valve may be supplemented by a well-known clamp 86 known as a Roberts clamp. In addition, the system may include a filter 88 and a further flow control valve or flow control orifice 90 such as a capillary tube.

Figure 18:
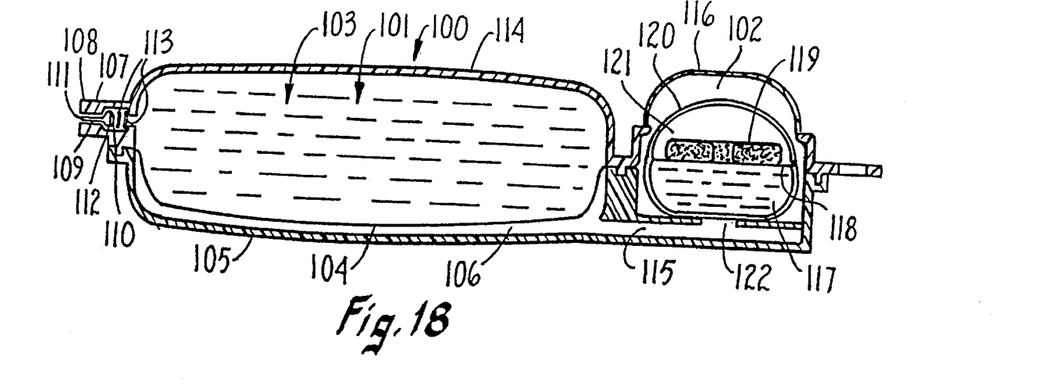
FIGS. 18 and 19 are cross-sectional side views of a preferred device in accordance with the present invention taken along line 18—18 in FIG. 16.
Figure 19:
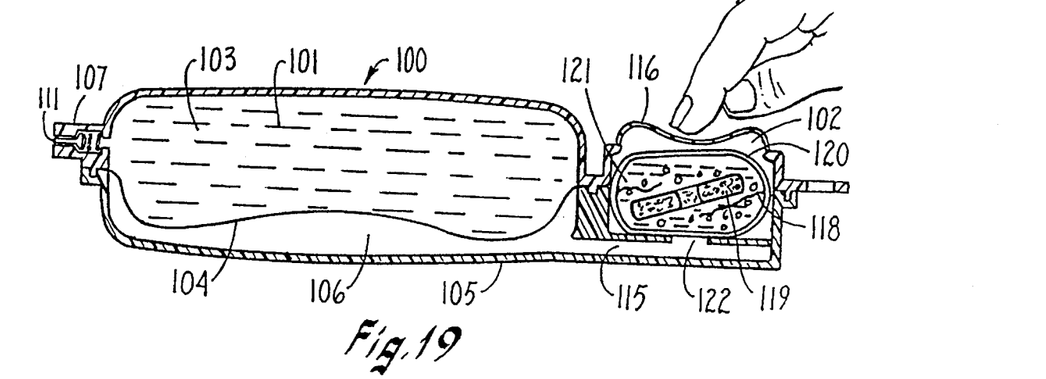
Figure 20A:
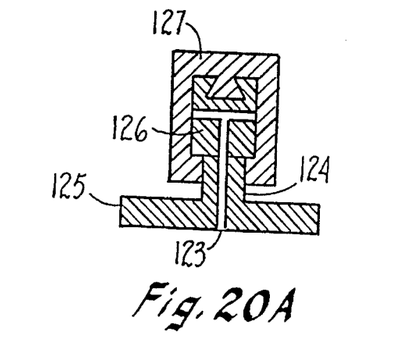
FIGS. 20A and 20B are schematics of a preferred pressure relief valve in accordance with the present invention.
Figure 20B:
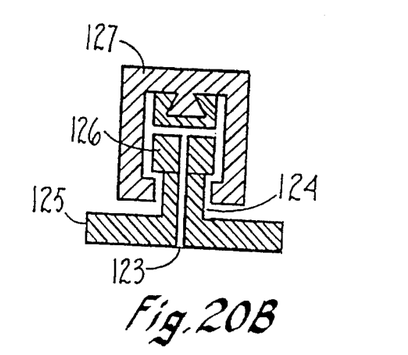

A highly preferred embodiment of the present invention is shown in FIGS. 18–20. For the purposes of this discussion, new reference numerals are assigned to like or similar parts described above. Referring first to FIG. 18, which is a cross-sectional side view of a preferred embodiment of the present invention taken along lines 18—18 of FIG. 17, where the device 100 is of a rectangular shape with rounded edges. It is separated into two separate compartments: the fluid delivery compartment 101 and the gas generation compartment 102. The fluid delivery compartment contains the liquid 103, that may contain a medication, that is to be delivered to a patient. Also within the fluid delivery compartment is the flexible membrane 104. The flexible membrane 104 is held in proximity to (or distended towards) the outer wall 105 in the lower section of the device 100 by the liquid 103. The flexible membrane 104 may contact the outer wall 105, or it may have a slight space 106 (as pictured).

Preferably, the liquid 103 is additionally kept within the fluid delivery compartment 101, by a one-way valve 107, that generally has an outer body 108 with an encircled plunger 109. The plunger 109 typically has a proximal end 110 and a distal end 111 (in relation to the fluid delivery compartment 101). The proximal end 110 of the plunger 109 is typically larger than the distal end 111. Further, the outer body 108 of the valve 107 has a concentric ridge 112 so that the larger proximal end 110 of the plunger 109 abuts the ridge 112, preventing the liquid 103 from flowing through the valve 107. Additionally, the valve 107 can have biasing means, such a spring 113, that forces the proximal end 110 of the plunger 109 distally toward the ridge 112, thereby further aiding in preventing the liquid 103 from flowing through the valve 107.

The valve 107 can be specially manufactured or can be a standard one-way luer fitting, such as those that are commercially available. For example, the Halkey-Roberts Corporation (St. Petersburg, Fla.) produces a variety of luer syringe check valves that can be used for this purpose. We prefer to use Halkey-Roberts Model No. V24200.

It is preferred that all materials that are in contact with the liquid 103 in the fluid delivery compartment 101, such as the flexible membrane 104, the wall 114, and the valve 107 (and it components) be constructed of materials that are non-leaching and are appropriate for medical use. One example of such a material is ultrapure polypropylene and other similar materials. In U.S. Pat. No. 4,803,102 one formulation of ultrapure polypropylene is described. Thinner preparations of ultrapure polypropylene (i.e., 0.002 to 0.010 inch gauge) are used in preparing the flexible membrane 104 and thicker gauge materials (i.e., molded to 0.030 to 0.060 inch gauge) are preferred for making the casing (defined by walls 105 and 114).

The gas generating compartment 102 is in fluid communication with the fluid delivery compartment 101 through a channel 115 and hole 122. Thus, when gas is generated in the gas generating compartment 102 it will travel through the channel 115 either filling or making the space 106 in the fluid delivery compartment 101. The gas generating compartment 102 additionally comprises a depressible member 116 which is sealingly joined to the case of the device 100. The depressible membrane sits above the gas generating compartment 102 inside the gas generating compartment 102 are the reactants for generating the gas. Shown in this embodiment is a liquid reactant 117 that in a preferred embodiment is contained within a breakable sack 118. Above the sack rests, in this embodiment, a solid reactant pellet 119.

In a highly preferred embodiment, the liquid reactant 117 is a solution of citric acid (7.5 gm/15 ml (2.6M)) and the solid reactant is a sodium carbonate "donut shaped" pellet, formed using a tablet or pill press of the shape shown in FIG. 2a. In the pellet, preferably 2.72 grams of sodium carbonate is mixed with 15% by weight of a filler, polyvinylpyrrolidone (PLASDONE, available from ISP Technologies, Inc., Wayne, N.J.) to make a 3.2 gm pellet. Moreover, preferably a room temperature vulcanizing (RTV) silicone adhesive was applied in strips, as shown in FIG. 2b, so as to reduce the surface area of the sodium carbonate and filler that would be exposed to the citric acid solution. In a preferred embodiment the RTV is PERMATEX®, available from Loctite Corporation, Cleaveland, Ohio (Part No. 66B).

Also, in this embodiment, the reactants are contained within a pouch 120. The pouch 120 in a highly preferred embodiment is composed of a hydrophobic material. Hydrophobic materials generally will contain liquids but will allow gases to pass, provided, some of their surface is not covered by a the liquid. Hydrophobic materials are typically formed from polymeric materials. Generally, they formed into a membrane. Examples of useful hydrophobic materials for preparing the pouch 120 are such materials as Tyvek® 1073B (Dupont), Versapel® 450 (Gelman), Goretex® 0.45μ polypropylene bucking, Celguard 2400 (Hoechst-Celanese), Porex® (a hydrophobic scintered polypropylene), and 3M BMF™ (Minnesota Mining and Manufacturing).

As will be understood, the use of a hydrophobic pouch 120 is very useful in that it contains the reactants within the gas generating chamber 102. This fact reduces concerns that the reactants could mix with the liquid in the fluid delivery compartment 101. However, it is critical to note that, as mentioned, the hydrophobic pouch 120 will release gas only so long as a gas pocket 121 exists. Therefore, the hydrophobic pouch must be carefully designed to ensure that the gas pocket 121 is maintained throughout the course of the reaction. If the gas pocket 121 were not present, the pouch 120 would burst and the contents (particularly the liquid reactant 117) of the gas generating compartment 102 would spill into the fluid delivery compartment 101 through the channel 115 and the hole 122. Since the liquid reactant 117 would no longer be in substantial contact with the solid reactant 119, the reaction would essentially terminate and limited additional gas would be evolved. However, as will be appreciated, because of the generation of gas through the reaction, there will be a tendency for the pouch 120 to reinflate and sparge gas, prior to failure.

An additional advantage to the use of the hydrophobic pouch is the fact that it enables the device 100 to be used in any orientation. The reactants in the gas generating chamber 102 are physically separated from the fluid delivery compartment 101 and the liquid 103, and no matter what orientation the device is moved to (so long as the gas pocket 121 exists) gas will continue to be delivered to the fluid delivery compartment 101. This makes the device 100 very versatile. For example, medical personnel do not have to carefully orient the device 100 and ambulatory patients can carry the device in their pockets.

It will be appreciated that the advantage associated with the hydrophobic pouch (i.e., allowing the orientation of the pump to be an insubstantial consideration since the chemical reactants will not get near the fluid to be delivered to the patient and allowing the chemical reactants to stay in contact with one another so as to continue the chemical reaction therebetween) can be achieved through a number of other mechanisms. In general, therefore, any mechanism that allows the gas generated by the reaction between the reactants to be communicated to the pump while the chemical reactants remain in contact away from the pump can be used. Non-limiting examples of such mechanisms include, in addition to the hydrophobic pouch mentioned above, placing the reactants in a float or on rollers in a container so that the reactants remain in the container despite the orientation; use of a hydrophobic membrane in a lumen in communication with a reactant chamber and a pump chamber; lining a container, otherwise sealed, with a hydrophobic material extending above any liquid level and providing a lumen from the container, behind the hydrophobic material, to communicate with the pump.

However, returning the embodiment shown in FIG. 19, in order to operate the pump in this embodiment, a user can simply depress the depressible membrane 116 down into the gas generating compartment 102 with their index finger, for example. This action will force the hydrophobic pouch 120 down onto the solid reactant 119. Such action will break the sack 118 that contained the liquid reactant 117. The chemicals will react and gas will be generated. Provided, as mentioned above, that the gas pocket 121 is maintained, gas will flow through the hydrophobic pouch 120 and be communicated through the hole 122 into the channel 115 and into the fluid delivery compartment 101. Thereafter, provided that the valve 107 is opened through manually depressing the distal end 111, proximally, liquid 103 will begin to flow through the valve 107. As gas continues to be generated the flexible membrane 104 will be displaced away from wall 105 increasing the size of the space 106 between the wall 105 and the flexible membrane 104 as the liquid 103 is delivered out of the device 100.

As an additional control feature and for safety, a preferred embodiment of the present invention further includes a pressure relief valve. A simple, but highly effective, pressure relief valve is shown in FIGS. 20A and 20B. The pressure relief valve is in communication with the gas generating chamber through a gas channel 123. The gas channel extends through the casing 125 of the device into a stem 124 that is topped by a mandrel 126. The mandrel 126 is topped by an elastomeric material 127 that concentrically and sealingly surrounds the mandrel 126. The elastomeric material is essentially similar to a silicone rubber septum that folds over, surrounds, and seals around the mandrel 126. While the system operates at preferably 10 psi or less, the elastomeric material 127 will not allow gas to escape. However, when the system exceeds 10 psi, the gas will force out the sides of the elastomeric material 127 allowing gas to escape.

Figure 21:
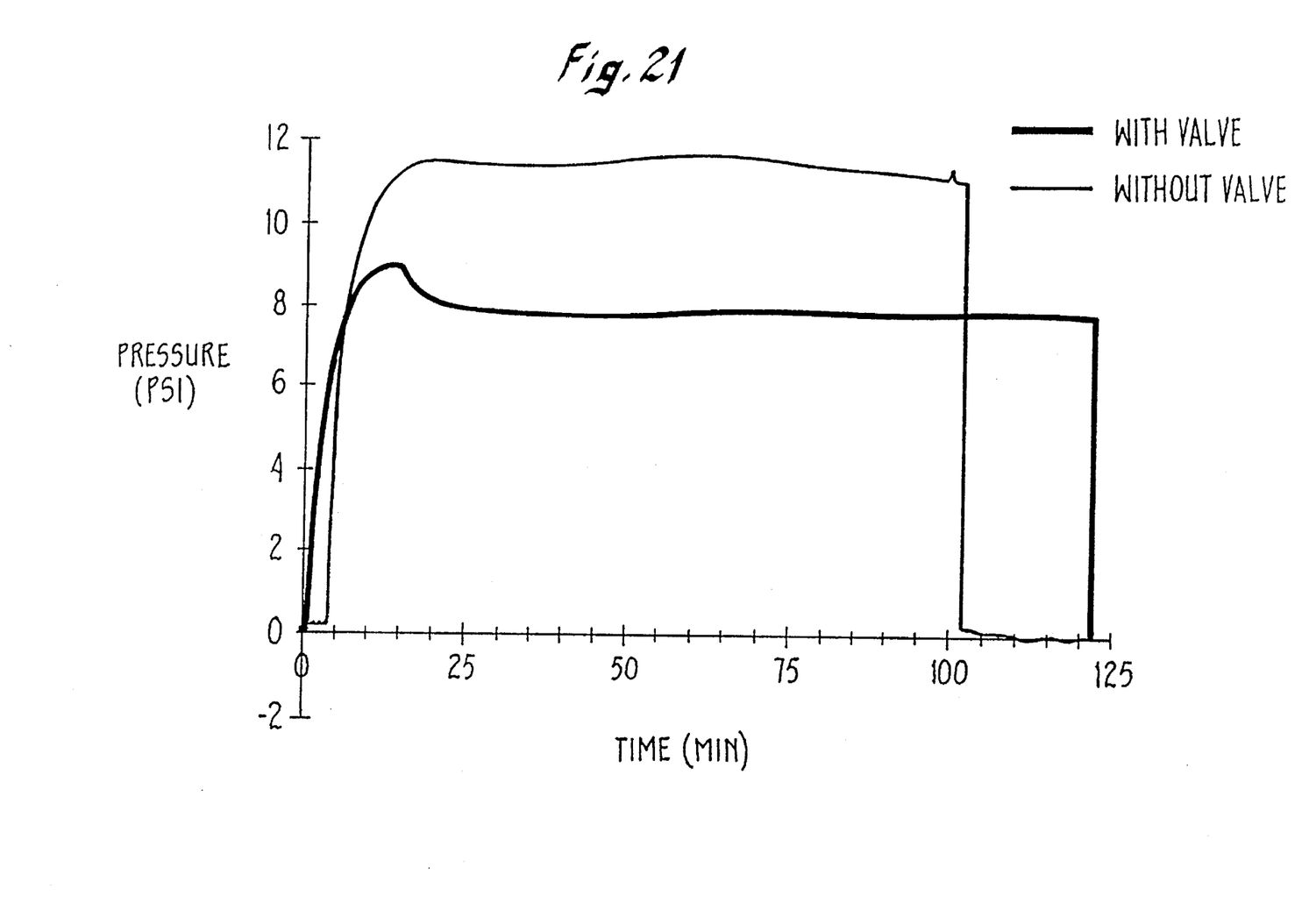
FIG. 21 is a graph showing the flow rate over time obtained in a device through the use of the reactants shown in connection with FIG. 1(iii) and the pressure relief valve of FIG. 20.

We have discovered that use of the pressure relief valve in combination with the citric acid/sodium carbonate, Plasdone, RTV pellets, as described above, we can achieve an almost completely linear pressure profile as is shown in FIG. 21. Such a linear pressure profile gives rise to an almost perfectly linear flow rate of fluid from the pump.

It will now also be appreciated that a variety of additional features could be added to the pressure relief valve of the present invention in order to lend greater control and conserve gas pressure. For example, the pressure relief valve shown in FIGS. 20A and 20B could be replaced by a balloon or other pressure/gas reserve mechanism. There are, for instance, inelastic balloon structures that do not show enhanced pressure at reduced diameters. Such materials could be attached to the mandrel 126 in FIGS. 20A to 20B to capture excess gas. As well, simple two way regulators can be readily conceived of by those of ordinary skill in the art to remove excess gas at a given pressure from the system and introduce gas back to the system when the pressure falls below a certain, predetermined pressure.

It will be evident from the above that there are many additional embodiments of this invention which, while not expressly described above, are clearly within the scope and spirit of the invention. The above description is therefore intended to be exemplary only and the invention is to be limited solely by the appended claims.

What we claim is:

1. A method for dispensing a liquid, comprising the steps of:

providing an infusion device having a liquid chamber and a propellant chamber, said chambers being separated by a flexible barrier, and wherein said chambers and said flexible barrier are enclosed in a casing, with a liquid suitable for infusion into a patient contained in said liquid chamber, and said liquid chamber having a port to the outside of said infusion device;

combining a solid chemical and a liquid chemical that are contained in a third chamber that is separate from said propellant and liquid chambers, said solid and liquid chemicals being reactive to form a propellant gas;

introducing said propellant gas from said third chamber into said propellant chamber and thereby pressurizing said liquid chamber by virtue of propellant gas pressure applied to said flexible barrier such that said liquid flows out of said liquid chamber through said port; and maintaining a controlled propellant gas pressure on said liquid chamber while said liquid is flowing out of said liquid chamber.

2. The method of claim 1, wherein said infusion device further comprises a pressure relief valve in fluid communication with said propellant chamber, and wherein said maintaining step further comprises venting said propellant gas through said pressure relief valve when said propellant gas pressure increases to a predetermimed pressure.

3. The method of claim 1, wherein said infusion device further comprises a hydrophobic material interposed between said propellant chamber and said first and second chemicals within said third chamber, and wherein said introducing step further comprises directing said propellant gas through said hydrophobic material into said propellant chamber.

4. The method of claim 1, wherein said maintaining step further comprises controlling the rate of said propellant gas generating reaction of said chemicals.

5. The method of claim 4, wherein said infusion device further comprises:

barrier means initially separating said first and second chemicals within said third chamber, and wherein said method further comprises the step of breaching said barrier to cause said first and second chemicals to come into contact and react to form said propellant gas.

6. The method of claim 4, wherein said infusion device further comprises a pressure relief valve in fluid communication with said propellant chamber, and wherein said maintaining step further comprises venting said propellant gas through said pressure relief valve when said propellant gas pressure increases to a predetermined pressure.

* * * * *

UNITED STATES PATENT AND TRADEMARK OFFICE
CERTIFICATE OF CORRECTION

PATENT NO. : 5,553,741

DATED : September 10, 1996

INVENTOR(S) : Gregory E. Sancoff, Mark C. Doyle and Frederic P. Field

It is certified that error appears in the above-indentified patent and that said Letters Patent is hereby corrected as shown below:

On the title page: Item [75] Inventors:

please delete "both of Calif." and please insert the following after "San Diego": -- Frederic P. Field, Solana Beach, all of Calif.--

Signed and Sealed this

Twenty-second Day of July, 1997

Attest:

BRUCE LEHMAN

*Attesting Officer*

*Commissioner of Patents and Trademarks*